(12) United States Patent
Mourelle Mancini et al.

(10) Patent No.: US 9,745,346 B2
(45) Date of Patent: Aug. 29, 2017

(54) ANTIMICROBIAL PEPTIDES AND THEIR APPLICATION

(71) Applicant: INFINITEC ACTIVOS S.L., Barcelona (ES)

(72) Inventors: Marisabel Mourelle Mancini, Barcelona (ES); Magdalena Carceller Margeli, Barcelona (ES); Luis Javier Cruz Ricondo, Barcelona (ES)

(73) Assignee: INFINITEC ACTIVOS S.L, Barcelona (ES)

( * ) Notice: Subject to any disclaimer, the term of this patent is extended or adjusted under 35 U.S.C. 154(b) by 0 days.

(21) Appl. No.: 15/118,884

(22) PCT Filed: Mar. 10, 2015

(86) PCT No.: PCT/EP2015/054883
§ 371 (c)(1),
(2) Date: Aug. 14, 2016

(87) PCT Pub. No.: WO2015/135896
PCT Pub. Date: Sep. 17, 2015

(65) Prior Publication Data
US 2017/0081364 A1    Mar. 23, 2017

(30) Foreign Application Priority Data
Mar. 10, 2014    (EP) .................................... 14382085

(51) Int. Cl.
| | | |
|---|---|---|
| A01N 37/18 | (2006.01) |
| A61K 38/00 | (2006.01) |
| A61P 31/04 | (2006.01) |
| C07K 7/06 | (2006.01) |
| A01N 37/44 | (2006.01) |

(52) U.S. Cl.
CPC ................ C07K 7/06 (2013.01); A01N 37/44 (2013.01); A61K 38/00 (2013.01)

(58) Field of Classification Search
CPC ........... A01N 37/44; A61K 38/00; C07K 7/06
See application file for complete search history.

(56) References Cited

U.S. PATENT DOCUMENTS

| | | | | |
|---|---|---|---|---|
| 5,652,332 A | | 7/1997 | Little, II | |
| 8,114,408 B2* | | 2/2012 | Choi ...................... | A61K 39/17 424/178.1 |

FOREIGN PATENT DOCUMENTS

EP    0976402 A2    2/2000

OTHER PUBLICATIONS

Betts et al. Amino Acid Properties and Consequences of Substitutions. Chapter 14. Bioinformatics for Geneticists, 2003. pp. 289-316.*

Barker, H., et al., "Formate Protects Stationary-Phase *Escherichia coli* and *Salmonella* cells from Killing by a Cationic Antimicrobial Peptide", "Molecular Microbiology", 2000, p. 1518-1529, vol. 35, No. 6.

Velucchi, M., et al., "Molecular Requirements of Peptide Structures Binding to the Lipid-A Region of Bacterial Endotoxins", "Vaccines", 1994, pp. 141-146, vol. 94, Publisher: Cold Spring Harbor Laboratory Press.

* cited by examiner

*Primary Examiner* — Marcela M Cordero Garcia
(74) *Attorney, Agent, or Firm* — Hultquist, PLLC; Mary B. Grant

(57) ABSTRACT

The present invention relates to a compound of formula (I) and to compositions comprising said compound, as well as the use of said compound and/or said compositions to prevent fungal and/or bacterial growth.

21 Claims, No Drawings

ANTIMICROBIAL PEPTIDES AND THEIR APPLICATION

CROSS-REFERENCE TO RELATED APPLICATIONS

This application is a U.S. national phase under the provisions of 35 U.S.C. §371 of International Patent Application No. PCT/EP15/54883 filed Mar. 10, 2015, which in turn claims priority of European Patent Application No. 14382085.0 filed Mar. 10, 2014. The disclosures of such international patent application and European priority patent application are hereby incorporated herein by reference in their respective entireties, for all purposes.

FIELD OF THE INVENTION

The present invention relates to novel antimicrobial peptides and to antimicrobial compositions comprising said peptides, as well as the use of said peptides and/or said compositions to prevent bacterial and/or fungal growth.

BACKGROUND OF THE INVENTION

In an effort to identify new antimicrobial compounds with a mechanism of action different to those of conventional antibiotics, both pharmaceutical and biotechnology companies have turned their attention to antimicrobial peptides.

Naturally-occurring antimicrobial peptides are evolutionary conserved components of the host's innate immunity system that form the first line of defense against infections. They have been identified in almost all classes of life. In this respect, antimicrobial peptides are generally defined as peptides with direct antibiotic activity, having fewer than about 50 amino acids and having a net positive charge. To date, more than 600 peptides (in virtually all species of life) have been described which not only kill pathogenic microorganisms, including Gram-positive and Gram-negative bacteria, viruses, protozoa and fungi, but also play a role in recruiting and promoting elements of the innate immune system.

The significant advantage of antimicrobial peptides resides in their mechanism of action, which is markedly different from that of conventional antibiotics. Although the precise mechanism of the broad spectrum of antimicrobial activity of these peptides is not yet fully understood, they appear to act via a specific, but not receptor-mediated, formation of transmembrane pores or ion channels on cellular membrane. This causes leakage of essential metabolites that results in the disruption of microbial cell structure and leads to cell death. In contrast to conventional antibiotics, they do not appear to induce microbial resistance and require only short time to induce killing. As the growing resistance of bacterial pathogens to conventional antibiotics has become serious global health problem, this alarming situation resulted in a search for novel alternative to traditional antibiotics such as antimicrobial peptides.

Given the complexity of microorganisms of potential or real pathogenicity to animals and humans, there is a clear need for a diverse range of effective antimicrobials e.g., having a broad spectrum or a spectrum of activity that complements existing therapeutics e.g., known antibiotics or antimicrobial proteins. There also remains a need for antimicrobial proteins having specific activity comparable to that of existing antibiotic treatments, preferably without the development of the resistance that occurs to conventional antibiotic compounds. There is also a need for antimicrobials that are effective in a wide range of applications, including the food, agriculture and horticulture industries, and in medicine, veterinary science and phytopathology. Clearly, it is highly desirable for any antimicrobial composition of matter to exhibit reduced toxicity and high activity at physiological conditions, e.g., at physiological salt concentrations. In addition, it would also be an advantage to have antimicrobial peptides with a low number of aminoacids as this would simplify its synthesis and purification.

SUMMARY OF THE INVENTION

The inventors have now discovered new synthetic peptides comprising only six aminoacids, which are capable of arresting bacterial and fungal growth at relatively low concentrations. More specifically, the peptides of the invention have shown minimum inhibitory concentrations in the order of 5-35 μg/ml against a variety of Gram-negative bacteria, in the order of 5-15 μg/ml against a variety of Gram-positive bacteria and in the order of 0.1-0.5 μg/ml against a variety of fungi.

Additionally the inventors have found that peptides of the present invention are capable of inhibiting the formation of bacterial biofilms and to reduce the amount of already formed bacterial biofilms.

In the first aspect, the present invention refers to a compound of formula (I):

$R_1$-Lys-Ala-Gln-Lys-Arg-Phe-$R_2$

($R_1$-SEQ ID NO: 1-$R_2$)            (I)

wherein $R_1$ is selected from the group consisting of H, $C_1$-$C_{24}$ alkyloyl, $C_2$-$C_{24}$ alkenyloyl and $C_6$-$C_{10}$ aryl;

$R_2$ is selected from the group consisting of —$OR_3$, —$SR_3$, —$NR_3R_4$, and —NH—$(CH_2)_3$—$(OCH_2CH_2)_n$—$CH_2$—$NH_2$ wherein n is an integer from 1 to 6;

$R_3$ and $R_4$ are independently selected from the group consisting of H; $C_1$-$C_6$ alkyl; $C_3$-$C_8$ cycloalkyl; $C_6$-$C_{10}$ aryl; $C_6$-$C_{10}$ aryl-$C_1$-$C_6$ alkyl; 5, 6 or 7 membered heterocycle containing 1, 2 or 3 heteroatoms in the ring independently selected from the group consisting of N, O and S; 5 or 6 membered monocyclic heteroaryl containing 1, 2, 3 or 4 heteroatoms in the ring independently selected from the group consisting of N, O and S; 8, 9 or 10 membered bicyclic heteroaryl containing 1, 2, 3 or 4 heteroatoms independently selected from the group consisting of N, O and S; heteroaryl-$C_1$-$C_3$ alkyl, wherein the heteroaryl is monocyclic or bicyclic as previously defined;

its stereoisomers, its cosmetically acceptable salts, or mixtures thereof.

In the second aspect, the invention refers to a composition which comprises a compound as defined in the first aspect, preferably a cosmetic composition comprising also a cosmetically acceptable excipient or a pharmaceutical composition comprising also a pharmaceutically acceptable carrier.

In the third aspect, the invention refers to a compound of formula (I) as defined in the first aspect, or a composition as defined in the second aspect, for use the prevention of bacterial and/or fungal growth when administered to a human or animal thereby finding use to prevent or to treat diseases associated with infection with bacteria or fungi.

In the fourth aspect, the invention refers to the use of a compound of formula (I) as defined in the first aspect, or composition as defined in the second aspect, for the manufacture of a medicament for the prevention of fungal and/or bacterial growth when administered to a human or animal.

In the fifth aspect, the invention relates to a method for the prevention of fungal and/or bacterial growth in a human or animal in need thereof, which comprises the administration of an effective amount of a compound of formula (I) as defined the first aspect, or composition as defined in the second aspect.

In the sixth aspect, the invention refers to the use of a compound of formula (I) as defined in the first aspect to prevent bacterial and/or fungal growth in a composition, preferably a pharmaceutical or a cosmetic composition or at an inanimate surface such as a medical device.

DETAILED DESCRIPTION OF THE INVENTION

The compounds of the invention may be prepared using conventional techniques of peptide synthesis in solid phase such as Fmoc-based chemistry described for example in Fmoc Solid Phase Peptide Synthesis: A Practical Approach edited by Weng C. Chan and Peter D. White. New York: Oxford University Press, 2000.

"Alkyl" refers to a straight or branched hydrocarbon chain radical consisting of carbon and hydrogen atoms, containing no unsaturation, having 1 to 16, preferably 1 to 6, more preferably 1 to 3 carbon atoms, and which is attached to the rest of the molecule by a single bond, e.g., methyl, ethyl, n-propyl, i-propyl, n-butyl, t-butyl, and n-pentyl.

"Alkyloyl" refers to a straight or branched hydrocarbon chain radical consisting of carbon and hydrogen atoms, containing no unsaturation, having 1 to 24, preferably 10 to 24 carbon atoms, and which is attached to the rest of the molecule by —C(O)— group, e.g., caproyl ($CH_3$—$(CH_2)_8$—C(O)—), lauroyl ($CH_3$—$(CH_2)_{10}$—C(O)—), myristoyl ($CH_3$—$(CH_2)_{12}$—C(O)—), palmitoyl (Palm) ($CH_3$—$(CH_2)_{14}$—C(O)—), stearoyl ($CH_3$—$(CH_2)_{16}$—C(O)—), arachidoyl ($CH_3$—$(CH_2)_{18}$—C(O)—) and behenoyl ($CH_3$—$(CH_2)_{20}$—C(O)—).

"Alkenyloyl" refers to a straight or branched hydrocarbon chain radical consisting of carbon and hydrogen atoms, containing one or more unsaturations, having 1 to 24, preferably 10 to 24 carbon atoms, and which is attached to the rest of the molecule by —C(O)— group, e.g., myristoleyl ($CH_3(CH_2)_3CH$=$CH(CH_2)_7C(O)$—), palmitoleyl ($CH_3(CH_2)_5CH$=$CH(CH_2)_7C(O)$—), oleyl ($CH_3(CH_2)_7CH$=$CH(CH_2)_7C(O)$—), and linoleyl ($CH_3(CH_2)_4CH$=$CHCH_2CH$=$CH(CH_2)_7C(O)$—).

"Aryl" refers to an aromatic hydrocarbon radical having 6 to 10 carbon atoms such as phenyl or naphthyl.

"Aryl-alkyl" refers to an alkyl radical, as defined above, attached to an aryl radical, as defined above, such as benzyl.

"Cycloalkyl" refers to a saturated carbocyclic ring having from 3 to 8 carbon atoms.

"Heteroaryl" refers to a 5 or 6 membered monocyclic aromatic ring or 8, 9 or 10 membered bicyclic aromatic ring, which contains carbon atoms and 1, 2, 3 or 4 heteroatoms in the ring independently selected from the group consisting of N, O and S, such as pyridine.

"Heteroarylalkyl" refers to an alkyl radical, as defined above, attached to a heteroaryl radical, as defined above.

"Heterocycle" refers to a 5, 6 or 7 membered, saturated or partially saturated ring, which contains carbons atoms and 1, 2 or 3 heteroatoms in the ring independently selected from the group consisting of N, O and S. Examples of heterocycles are benzimidazole, benzothiazole, furan, isothiazole, imidazole, indole, piperidine, piperazine and morpholine.

"Stereoisomer" refers to compound consisting of the same atoms attached with the same bond sequence but having different tridimensional structures that cannot be interchanged, such as R/S and cis/trans (Z/E) configuration.

The term "cosmetically acceptable salts" means a salt recognized for its use in human beings, and includes salts used to form base addition salts, either inorganic or organic, or acid addition salts, either inorganic or organic. It is to be noted that, since safety requirements for pharmaceuticals are more stringent than those for cosmetics, any pharmaceutically acceptable salt will also be a cosmetically acceptable salt. The nature of the salt is not critical, provided that it is cosmetically or pharmaceutically acceptable. The cosmetically or pharmaceutically acceptable salts of the peptides of the invention can be obtained by the conventional methods, well known in the prior art [Berge S. M. et al., "Pharmaceutical Salts", (1977), J. Pharm. Sci., 66, 119].

Additionally, it will be appreciated that non-cosmetically acceptable salts also fall within the scope of the invention since said non-cosmetically acceptable salts may be useful precursors in the preparation of cosmetically acceptable salts. The preparation of salts can be carried out by methods known in the art. For instance, cosmetically acceptable salts of compounds provided herein may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, ammonium, and organic alkali salts such as, for example, ethylenediamine, ethanolamine, N,N-dialkylenethanolamine, triethanolamine, glucamine and basic aminoacids salts. Examples of the metallic salts include, for example, sodium, potassium, calcium, magnesium, aluminium and lithium salts.

"Cosmetically acceptable excipients" refer to excipients that are physiologically tolerated and that do not produce any undesired allergic or similar reaction when topically applied to a human, in particular when applied to the skin, scalp, hair or nails. Preferably, as used herein, it means that said excipient is included in the European Commission database for cosmetic substances an ingredients CosIng.

In this description the abbreviations used for amino acids follow the recommendations of the 1983 IUPAC-IUB Commission of Biochemical Nomenclature specified in Eur. J. Biochem., (1984), 138, 937.

Thus, for example, Arg or R represents $NH_2$—CH($CH_2$—$CH_2$—$CH_2$—NH—C(=NH)$NH_2$)—COOH, Arg- or R— represents $NH_2$—CH($CH_2$—$CH_2$—$CH_2$—NH—C(=NH)$NH_2$)—CO—, -Arg or —R represents —NH—CH($CH_2$—$CH_2$—$CH_2$—NH—C(=NH)$NH_2$)—COOH, and -Arg- or —R— represents —NH—CH($CH_2$—$CH_2$—$CH_2$—NH—C(=NH)$NH_2$)—CO—. Therefore, the hyphen, which represents the peptide bond, eliminates the OH in the 1 carboxyl group of the amino acid (represented here in the conventional non-ionized form) when situated to the right of the symbol, and eliminates the H of the 2 amino group of the amino acid when situated to the left of the symbol; both modifications can be applied to the same symbol (see Table 1).

The aminoacids are named using the conventional nomenclature in one and three letter codes, as follows:
alanine, Ala o A,
phenylalanine, Phe o F,
lysine, Lys o K,
glutamine, Gln o Q,
arginine, Arg o R.

In the first aspect, the invention refers to a compound of formula (I), as defined above.

Preferably $R_1$ is selected from the group consisting of H, $C_{10}$-$C_{24}$ alkyloyl and $C_{10}$-$C_{24}$ alkenyloyl; more preferably from the group consisting of caproyl ($CH_3$—($CH_2$)$_8$—C(O)—), lauroyl ($CH_3$—($CH_2$)$_{10}$—C(O)—), myristoyl ($CH_3$—($CH_2$)$_{12}$—C(O)—), palmitoyl ($CH_3$—($CH_2$)$_{14}$—C(O)—), stearoyl ($CH_3$—($CH_2$)$_{16}$—C(O)—), arachidoyl ($CH_3$—($CH_2$)$_{18}$—C(O)—) and behenoyl ($CH_3$—($CH_2$)$_{20}$—C(O)—); still more preferably, $R_1$ is palmitoyl.

Preferably $R_2$ is selected from the group consisting of —$OR_3$, —$SR_3$, —$NR_3R_4$, wherein $R_3$ and $R_4$ are independently selected from the group consisting of H and $C_1$-$C_6$ alkyl and —NH—($CH_2$)$_3$—($OCH_2CH_2$)$_n$—$CH_2$—$NH_2$ wherein n is an integer from 1 to 6; more preferably $R_2$ is selected from the group consisting of —OH, —SH, —$NH_2$ and —NH—($CH_2$)$_3$—($OCH_2CH_2$)$_n$—$CH_2$—$NH_2$ wherein n is an integer from 1 to 6; still more preferably $R_2$ is $NH_2$ or —NH—($CH_2$)$_3$—($OCH_2CH_2$)$_3$—$CH_2$—$NH_2$.

In a preferred embodiment, $R_1$ is palmitoyl and $R_2$ is —$NH_2$, i.e., the compound of formula (I) is a peptide having the sequence Palm-Lys-Ala-Gln-Lys-Arg-Phe —$NH_2$, (Palm-SEQ ID NO: 1—$NH_2$).

In a preferred embodiment, the compound of formula (I) is one of:
Palm-Lys-Ala-Gln-Lys-Arg-Phe —$NH_2$(Palm-SEQ ID NO: 1—$NH_2$)
Ac-Lys-Ala-Gln-Lys-Arg-Phe —$NH_2$(Ac-SEQ ID NO: 1—$NH_2$)
Palm-Lys-Ala-Gln-Lys-Arg-Phe —NH—($CH_2$)$_3$—($OCH_2CH_2$)$_3$—$CH_2$-$NH_2$ (Palm-SEQ ID NO: 1—NH—($CH_2$)$_3$—($OCH_2CH_2$)$_3$—$CH_2$-$NH_2$).

In the second aspect, the invention refers to a cosmetic composition comprising a compound as previously defined and a cosmetically acceptable excipient.

In a preferred embodiment the cosmetically acceptable excipient(s) is(are) selected from the group consisting of humectants, emollients, rheological modifiers, perfumes, essential oils, preserving agents, solvents, emulsifiers, silicones, antioxidants, chelating agents, vitamins and mixtures thereof.

The composition of the invention may comprise humectants for preserving the moisture of the composition. Humectants in the context of the present invention may be selected, among other, from polyols, such as glycerol, glycerol polymers, diols, polyethylene glycols, alcoholic sugars, sugars, other polyols, and mixtures thereof. Examples of moistening agents are glycerol (1,2,3-propanetriol), propylene glycol, glycols, polyethylene glycols and mixtures thereof.

"Glycerin" or "glycerol" refers to 1,2,3-propanetriol.

"Glycerin polymers" refers to compounds having from 3 to 40 glycerin units, such as polyglycerin-3, polyglycerin-4, polyglycerin-6, polyglycerin-10, polyglycerin-20 y polyglycerin-40.

"Diols" define $C_2$-$C_4$ alkyls substituted with two hydroxyl groups. Examples of diols are butylene glycols such as 1,2-butanediol, 1,3-butanediol, 1,4-butanediol and 2,3-butanediol.

"Polyethylene glycol" or "PEG" refers to an oligomer or polymer of ethylene oxide having from 4 to 240 units of ethylene glycol, such as PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240; methoxylated polyethylene glycols, such as methoxy PEG-7, methoxy PEG-10, methoxy PEG-16, methoxy PEG-25, methoxy PEG-40, methoxy PEG-100; and glycerin polyethylene glycols, i.e., glycerin that has been etherified with 7 to 40 units of ethylene glycol, such as glycereth-7, glycereth-8, glycereth-12, glycereth-18, glycereth-20, glycereth-26 and glycereth-31.

"Alcoholic sugars" refers to polyols having the general formula $H(HCO)_{n+1}H$, such as erythritol, isomalt, lactitol, maltitol, mannitol, sorbitol and xylitol.

"Sugars" refers to monosaccharides and polysaccharides, such as amylose, fructose, glucose, mannose, lactose, ribose, saccharose, trehalose and xylose.

The composition according to the invention may comprise emolients for smoothening the skin. In the context of the present invention, emolients may be selected, among others, from alkanes and esters, such as glycerides, propylene glycol esters, alkyl esters, ethers, glycols, and mixtures thereof. Examples of emolients are cocoglycerides, $C_{12}$-$C_{15}$ alkyl benzoate, glycols, polyethylene glycols, ethers, glycerides, caprilates, $C_{12}$-$C_{15}$ alkyls.

"Glycerides" refers to mono, di and triesters of glycerin with acids, such as monoglycerides, for examples, glyceryl adipate, glyceryl caprate, glyceryl caprilate, glyceryl cocoate, glyceryl ethylhexanate, glyceryl heptanate, glyceryl isostearate, glyceryl lanolate, glyceryl laurate, glyceryl linoleate, glyceryl linolenate, glyceryl myristate, glyceryl oleate, and glyceryl palmitate; diglycerides, for example, glyceryl diisopalmitate, glyceryl diisostearate, glyceryl dilaurate, glyceryl dilinoleate, glyceryl dimyristate, glyceryl dioleate, glyceryl dipalmitate, and glyceryl distearate; triglycerides, for example $C_{10}$-$C_{16}$ triglycerides, $C_{18}$-$C_{36}$ triglycerides, and coco triglycerides; and mixed glycerides, such as glyceryl caprilate/caprate, glyceryl palmitate/lactate, glyceryl palmitate/stearate, glyceryl citrate/stearate, glyceryl stearate/diacetate, glyceryl stearate/lactate, glyceryl stearate/succinate, glyceryl acetate/stearate, glyceryl stearate/malate, glyceryl stearate/maleate, glyceryl cocoate/citrate/lactate, glyceryl ethylhexanate/stearate/adipate, glyceryl isostearate/myristate, glyceryl laurate/oleate, caprilate/caprate/cocoate glycerides, caprilate/caprate/laurate triglycerides, caprilate/caprate/linoleate triglycerides, caprilate/caprate/myristate/stearate triglycerides, caprilate/caprate/stearate triglycerides, caprilate/caprate/succinate triglycerides, oleate/linoleate triglyceride, and dicaprilate/dicaprate glycerides; among others.

Propylene glycol esters, such as propylene glycol dicaprilate/dicaprate, which is a mixed diester of propylene glycol and a combination of $C_8$-$C_{10}$ fatty acids, may also be used as emolients.

"Alkyl esters" refers to compounds that may be obtained by the esterification of an alkanol and an acid, such as alkyl $C_{12}$-$C_{15}$ benzoates; alkyl $C_{12}$-$C_{15}$ lactates; methyl esters, for example methyl caproate, methyl caprilate, methyl cocoate, methyl caprilate/caprate, methyl laurate, methyl linoleate, methyl myristate, methyl oleate, methyl palmate, methyl palmitate, and methyl stearate; ethyl esters, for examples ethyl caprate, ethyl isostearate, ethyl laurate, ethyl linoleate, ethyl linolenate, ethyl myristate, ethyl oleate, ethyl palmate, ethyl palmitate, and ethyl stearate; isopropyl esters, for examples isopropyl isostearate, isopropyl lanolate, isopropyl laurate, isopropyl linoleate, isopropyl myristate, isopropyl oleate, isopropyl palmitate, and isopropyl stearate; butyl ester, for example butyl isostearate, butyl myristate, butyl oleate, and butyl stearate; isobutyl esters, for example isobutyl myristate, isobutyl palmitate, and isobutyl stearate; hexyl esters, for example hexyl isostearate and hexyl laurate; isohexyl esters, for examples isohexyl caprate, isohexyl laurate, isohexyl neopentanoate, and isohexyl palmitate; cetyl esters, for example cetyl ethylhexanoate, cetyl caprilate, cetyl isononanoate, cetyl lactate, cetyl laurate, cetyl myristate, cetyl oleate, cetyl palmitate, cetyl ricinoleate, and cetyl stearate; isocetyl esters, for example isocetyl ethylhexanoate, isocetyl isodecanoate, isocetyl isostearate, isocetyl laurate, isocetyl myristate, isocetyl palmitate, and isocetyl stearate; cetearyl esters for example cetearyl ethylhexanoate, cetearyl isononanoate, cetearyl nonanoate, cetearyl palmate, and cetearyl palmitate; decyl esters, for example decyl castorate, decyl cocoate, decyl isostearate, decyl myristate, decyl oleate, decyl palmitate, and decyl succinate; isodecyl esters, for example isodecyl citrate, isodecyl cocoate, isodecyl ethylhexanoate, isodecyl isononanoate, isodecyl laurate, isodecyl myristate, isodecyl neopentanoate, isodecyl oleate, isodecyl palmitate, and isodecyl stearate; ethylhexyl esters, for example ethylhexyl benzoate, ethylhexyl caprilate/caprate, ethylhexyl cocoate, ethylhexyl ethylhexylhexanoate, ethylhexyl isononanoate, ethylhexyl isopalmitate, ethylhexyl isostearate, ethylhexyl laurate, ethylhexyl myristate, ethylhexyl neopentanoate, ethylhexyl oleate, ethylhexyl palmitate, and ethylhexyl stearate; hexyldecyl esters, for example, hexyldecyl benzoate, hexyldecyl ethylhexanoate, hexyldecyl hexyldecanoate, hexyldecyl laurate, hexyldecyl oleate, and hexyldecyl stearate; isostearyl esters, for example isostearyl acetate, isostearyl benzoate, isostearyl ethylhexanoate, isostearyl isononanoate, isostearyl isostearate, isostearyl lactate, isostearyl laurate, isostearyl linoleate, isostearyl myristate, isostearyl neopentanoate, and isostearyl palmitate; lauryl esters, for example lauryl cocoate, lauryl ethylhexanoate, lauryl isostearate, lauryl lactate, lauryl myristate, lauryl oleate, lauryl palmitate, and lauryl stearate; myristyl esters, for example myristyl acetate, myristyl ethylhexanoate, myristyl isostearate, myristyl lactate, myristyl myristate, myristyl neopentanoate, myristyl propionate, and myristyl stearate; octyldecyl esters, for example octyldecyl benzoate, octyldecyl cocoate, octyldecyl ethylhexanoate, octyldecyl lactate, octyldecyl myristate, octyldecyl neodecanoate, octyldecyl neopentanoate, octyldecyl oleate, and octyldecyl stearate; oleyl esters, for example oleyl acetate, oleyl lactate, oleyl lanolate, oleyl linoleate, oleyl myristate, oleyl oleate, and oleyl stearate; and stearyl esters, for example stearyl acetate, stearyl benzoate, stearyl caprilate, stearyl citrate, stearyl lactate, stearyl linoleate, and stearyl stearate; among others.

The esters may be further linked to polyethylene glycol and/or polypropylene glycol units.

"Alkanes" refers to linear or branched hydrocarbon chains having from 12 to 28 carbon atoms.

"Glycols" refers to "diols" and "polyethylene glycols" as previously defined.

"Ethers" may be selected from, among others, dicaprilyl ether, distearylether, as well as ethers linked to polyethylene glycol and/or polypropylene glycol units, such as, stearyl PPG-15 ether, butyl PPG-14 ether, myristyl PPG-3 ether, among other.

The composition according to the invention may comprise rheological modifiers for increasing or decreasing the viscosity thereof. Rheological modifiers, in the context of the present invention, may be selected from, among others, carbomers, acrylates, celluloses, xanthans, dextrans and mixtures thereof. Examples of rheological modifiers are sodium hydroxyethylacrylate/acryloyldimethyltaurate copolymer, carbomers, acrylates, xanthans, dextrans and celluloses.

"Carbomers" refers to high molecular weight polymers of acrylic acid, they may be homopolymers, and they may also be cross-linked with a pentaerythritol allyl ether, saccharose allyl ether or propylene allyl ether. Examples of carbomers are carbomer, potassium carbomer, sodium carbomer, calcium and potassium carbomer, TEA carbomer and hydroxypropylethylenediamine carbomer, among others.

"Acrylates" or "(meth)acrylates" may be selected from sodium hydroxyethylacrylate/acryloyldimethyltaurate copolymer, acrylates/beheneth-25 methacrylate copolymer, acrylates/$C_{10}$-$C_{30}$-alkylacrylate copolymer, acrylates/ceteth-20 itaconate copolymer, acrylates/ceteth-20 methacrylate copolymer, acrylates/diacetoneacryl amide copolymer, acrylates/laureth-25 methacrylate copolymer, acrylates/methoxy PEG-15 methacrylate copolymer, acrylates/palmeth-25 acrylate copolymer, acrylates/palmeth-25 itaconate copolymer, acrylates/steareth-20 itaconate copolymer, acrylates/steareth-20 methacrylate copolymer, acrylates/steareth-50 acrylate copolymer, methacrylates/stearylmethacrylate copolymer, sodium acrylate/sodium acryloyldimethyltaurate copolymer, sodium acrylate/sodium acryloyldimethyltaurate/acrylamide copolymer, sodium acrylate/vinyl alcohol copolymer, sodium acrylate/vinylacetamide copolymer, sodium acrylates copolymer, sodium acrylates/acrolein copolymer, starch/acrylates/acrylamide copolymer, cross-linked sodium acrylate polymers, cross-linked sodium acrylate/acryloyldimethyltaurate/dimethylacrylamide polymers, and $C_{10}$-$C_{30}$ alkyl polyacrylate, polyacrylates, among others.

"Celluloses" may be selected from cellulose, methylcellulose, ethylcellulose, hydroxypropylmethylcellulose, hydroxypropylcellulose, methyl ethyl cellulose, and microcrystalline cellulose, among others.

"Xanthans" may be selected from xanthan gum, hydroxypropyltrimonium xanthan gum, among others.

"Dextrans" may be selected from dextran, carboxymethyldextran, sodium carboxymethyldextran, and sodium salt dextran sulfate.

The composition according to the invention may comprise perfumes and essential oils, such as any fragrance substance commonly used in the field of cosmetics and lavender, jasmine, rose, eucalyptus, citronella, sandalwood, vetiver, lemon, orange, bergamot, musk essential oils.

Although it is not a preferred embodiment, the composition according to the invention may comprise preserving agents other than the peptides of the invention to further improve the prevention of microorganism growth therein. Preserving agents may be selected from, among other, phenols, phenoxy derivatives, heterocyclic derivatives, tropolone, ethylhexylglycerin, and mixtures thereof. Examples of preserving agents are phenoxyethanol, tropolone, chlorophenesin, ethylhexylglycerin, isothiazolidone, diazolidinylurea and parabens.

"Phenols" and "phenoxy derivatives" may be selected from parabens, such as methylparaben, ethylparaben, propylparaben, isopropylparaben, butylparaben, isobutylparaben, phenylparaben, potassium paraben, potassium methylparaben, potassium ethylparaben, potassium propylparaben, potassium butylparaben, sodium paraben, sodium methylparaben, sodium ethylparaben, sodium propylparaben, sodium isopropylparaben, sodium isobutylparaben, hexamidine diparaben, and hexamidine paraben; phenoxyethanol; phenoxyi sopropanol; chlorophenesin; chlorophene; bromochlorophene; triclosan; chloroxylenol; climbazole; isopropylcresol; salicylic acid; calcium salicylate; magnesium salicylate; potassium salicylate; sodium salicylate; salicylate-MEA (salicylic acid and 2-aminoethanol 1:1); salicylate-TEA (salicylic acid and 2,2',2''-nitrilotriethanol 1:1); p-chloro-m-cresol; potassium o-phenylphenate, and sodium o-phenylphenate; among others.

"Heterocyclic derivatives" may be selected from isothiazolinones, such as methylisothiazolinone and methylchloroisothiazolinone; diazolidinylurea; 5-bromo-5-nitro-1,3-dioxane and dimethyloxazolidine; among other.

The composition according to the invention may comprise solvent for dissolving other substances comprised therein. Common solvents in the context of the present invention may be selected from, among other, water, oleyl alcohol, ethoxydiglycol, ethyl alcohol, isopropyl alcohol, benzyl alcohol, and mixtures thereof.

The composition according to the invention may comprise emulsifiers for promoting the formation of intimate mixtures of non-miscible liquids by altering the interfacial tension. Emulsifiers, in the context of the present invention, may be selected from, among others, polysorbates, sorbitan esters, ethoxylated fatty alcohols, and mixtures thereof.

"Polysorbates" refer to PEG-ylated derivatives of sorbitan that are esterified with fatty acids, such as polysorbate 20, polysorbate 21, polysorbate 40, polysorbate 60, polysorbate 61, polysorbate 65, polysorbate 80, polysorbate 81, and polysorbate 85, among others.

"Sorbitan esters" may be selected from sorbitan caprylate, sorbitan cocoate, sorbitan diisostearate, sorbitan dioleate, sorbitan isostearate, sorbitan laurate, sorbitan oleate, sorbitan olivate, sorbitan palmitate, sorbitan sesquiisostearate, sorbitan sesquioleate, sorbitan stearate, sorbitan triisostearate, sorbitan trioleate, sorbitan tristearate, and sorbitan undecylenate, among others.

"Ethoxylated fatty alcohols" may be selected from ethoxylated derivatives of behenyl alcohol, such as beneth-2, beneth-5, beneth-10, beneth-15, beneth-20, beneth-25, and beneth-30, among others; $C_{11-13}$ pareth-10, $C_{11-13}$ pareth-6, $C_{11-13}$ pareth-9, $C_{11-15}$ pareth-12, $C_{11-15}$ pareth-15, $C_{11-15}$ pareth-20, $C_{11-15}$ pareth-3, $C_{11-15}$ pareth-30, $C_{11-15}$ pareth-5, $C_{11-15}$ pareth-7, $C_{11-15}$ pareth-9, $C_{11-21}$ pareth-10, $C_{11-21}$ pareth-3, $C_{12-13}$ pareth-10, $C_{12-13}$, pareth-15, $C_{12-13}$ pareth-2, $C_{12-13}$ pareth-23, $C_{12-13}$ pareth-3, $C_{12-13}$ pareth-4, $C_{12-13}$ pareth-5, $C_{12-13}$ pareth-6, $C_{12-13}$ pareth-7, $C_{12-13}$ pareth-9, $C_{12-14}$ pareth-12, $C_{12-14}$ pareth-3, $C_{12-14}$ pareth-7, $C_{12-15}$ pareth-10, $C_{12-15}$ pareth-11, $C_{12-15}$ pareth-12, $C_{12-15}$ pareth-2, $C_{12-15}$ pareth-3, $C_{12-15}$ pareth-4, $C_{12-15}$ pareth-5, $C_{12-15}$ pareth-7, $C_{12-15}$ pareth-9, $C_{12-16}$ pareth-5, $C_{12-16}$ pareth-7, $C_{12-16}$ pareth-9, $C_{14-15}$ pareth-11, $C_{14-15}$ pareth-12, $C_{14-15}$ pareth-13, $C_{14-15}$ pareth-4, $C_{14-15}$ pareth-7, $C_{20-22}$ pareth-30, $C_{20-40}$ pareth-24, $C_{20-40}$ pareth-3, $C_{20-40}$ pareth 40, $C_{22-24}$ pareth-33, $C_{30-50}$ pareth-10, $C_{30-50}$ pareth-3, $C_{30-50}$ pareth-40, $C_{40-60}$ pareth-10, $C_{40-60}$ pareth-3, $C_{9-11}$ pareth-3, $C_{9-11}$ pareth-4, $C_{9-11}$ pareth-6, $C_{9-11}$ pareth-8, $C_{9-15}$ pareth-8; ethoxylated derivatives of cetearyl alcohol, such as ceteareth-10, ceteareth-11, ceteareth-12, ceteareth-13, ceteareth-14, ceteareth-15, ceteareth-16, ceteareth-17, ceteareth-18, ceteareth-2, ceteareth-20, ceteareth-22, ceteareth-23, ceteareth-24, ceteareth-25, ceteareth-27, ceteareth-28, ceteareth-29, ceteareth-3, ceteareth-30, ceteareth-33, ceteareth-34, ceteareth-4, ceteareth-5, ceteareth-50, ceteareth-6, ceteareth-60, ceteareth-7, ceteareth-8, and ceteareth-9, among others; ethoxylated derivatives of cetyl alcohol, such as ceteth-1, ceteth-10, ceteth-12, ceteth-13, ceteth-14, ceteth-15, ceteth-16, ceteth-17, ceteth-18, ceteth-2, ceteth-20, ceteth-23, ceteth-24, ceteth-25, ceteth-3, ceteth-30, ceteth-4, ceteth-5, ceteth-6, and ceteth-7, among others; ethoxylated derivatives of cetoleyl alcohol, such as cetoleth-10, cetoleth-11, cetoleth-15, cetoleth-18, cetoleth-2, cetoleth-20, cetoleth-22, cetoleth-4, cetoleth-5, and cetoleth-6, among others; ethoxylated derivatives of decanol, such as deceth-10, deceth-3, deceth-4, deceth-5, deceth-6, deceth-7, deceth-8, and deceth-9, among others; ethoxylated derivatives of lauryl alcohol, such as laureth-1, laureth-10, laureth-11, laureth-13, laureth-14, laureth-15, laureth-16, laureth-2, laureth-20, laureth-23, laureth-25, laureth-3, laureth-30, laureth-4, laureth-6, laureth-7, laureth-8, and laureth-9, among others; ethoxylated derivatives of myristyl alcohol, such as myreth-10, myreth-2, myreth-3, myreth-4, and myreth-5, among others; ethoxylated derivatives of oleyl alcohol, such as oleth-10, oleth-11, oleth-12, oleth-15, oleth-16, oleth-2, oleth-3, oleth-30, oleth-35, oleth-4, oleth-40, oleth-45, oleth-5, oleth-6, oleth-7, oleth-8, and oleth-9, among others; and ethoxylated derivatives of stearyl alcohol such as steareth-1, steareth-10, steareth-11, steareth-13, steareth-14, steareth-15, steareth-16, steareth-2, steareth-20, steareth-200, steareth-21, steareth-25, steareth-3, steareth-4, steareth-5, steareth-6, steareth-7, and steareth-8, among others.

The composition according to the invention may comprise silicones such as aminoethylaminopropyl dimethicone, aminopropyl dimethicone, behenyl dimethicone, bis(aminopropyl) dimethicone, bis(hydroxyethoxypropyl) dimethicone, bis(mercaptopropyl) dimethicone, bis-PEG(1-20) dimethicone, $C_{20-24}$ alkyl dimethicone, $C_{24-28}$ alkyl dimethicone, cetyl dimethicone, diphenyl dimethicone, diphenylisopropyl dimethicone, hexyl dimethicone, hydroxypropyl dimethicone, stearyl dimethicone, vinyl dimethicone, $C_{24-28}$ alkyl methicone, $C_{26-28}$ alkyl methicone, $C_{30-45}$ alkyl methicone, stearyl methicone, among others.

The composition according to the invention may comprise antioxidants for inhibiting reactions promoted by oxygen, thus avoiding oxidation and rancidity of the composition. Common oxidants in the context of the present invention may be selected from, among others, vitamins C and E and derivatives thereof, such as tocopherol (vitamin E), ascorbic acid (vitamin C), and ascorbyl palmitate, among others; as well as weak organic acids, such as citric acid, among others.

The composition according to the present invention may comprise chelating agents such as 2,6-dicarboxypyridine; EDTA (ethylendiaminotetraacetic acid) and its salt, such as the calcium disodium salt, diammonium salt, dipotassium salt, disodium salt; cyclodextrin; oxalic acid and its derivatives, such as dimethyl oxalate, diethyl oxalate, dibutyl oxalate, diisobutyl oxalate, diisopropyl oxalate, dilithium oxalate, dipotassium oxalate, disodium oxalate; citric acid and its derivatives, such as acetyltrihexyl citrate, potassium citrate, among others.

The composition according to the invention may comprise vitamins such as vitamins A, C, D, and E.

In a particular embodiment, the compound of formula (I) represents from 0.0001% to 5% by weight with respect to the total weight of the composition.

In a particular embodiment, the composition of the invention comprises:

compound of formula (I) from 1% to 5% by weight, with respect to the total weight of the composition,
additional preserving agents from 0% to 5%,
vitamins from 0% to 20%,
solvents, rheological modifiers, emollients, emulsifiers and silicones from 0% to 20%,
perfumes and essential oils from 0% to 2%, and
antioxidants and chelating agents from 0% to 5%.

In another preferred embodiment, the compound of formula (I) is incorporated into a cosmetically acceptable vehicle or sustained release system selected from the group consisting of liposomes, millicapsules, microcapsules, nanocapsules, sponges, vesicles, micelles, millispheres, microspheres, nanospheres, microemulsions, nanoemulsions, milliparticles, microparticles, nanoparticles, and solid lipid nanoparticles, they are incorporated into hydrolyzed vegetal, animal or synthetic proteins, or are adsorbed onto a cosmetically acceptable solid support selected from the group consisting of talc, bentonite, silica, starch and maltodextrin, dextran and its derivatives.

"Sustained release" refers to a delivery system of a compound which provides the gradual release of said compound during a period of time and preferably, although not necessarily, with relatively constant compound release levels over a long period of time. Examples of delivery or sustained release systems are liposomes, millicapsules, microcapsules, nanocapsules, sponges, vesicles, micelles, millispheres, microspheres, nanospheres, microemulsions, nanoemulsions, milliparticles, microparticles, nanoparticles, and solid lipid nanoparticles.

The prefix "milli" refers to structures having a size comprised between 1 mm and 1000 mm. The prefix "micro" refers to structures having a size comprised between 1 μm and 1000 μm. The prefix "nano" refers to structures having a size comprised between 1 nm and 1000 nm.

"Vesicle" refers to a system that is formed naturally comprising a bilayered phospholipid membrane which contains a hydrophilic part and a hydrophobic part. If the vesicle is prepared artificially it is known as a "liposome".

The term "capsules" in combination with any of the previously defined prefixes refers to capsules made of biodegradable polymers, wherein biodegradable polymers are dextran, polylactide and polyglycolic, chondroitin sulfate, polyesters, polyethylene glycols, polycarbonates, polyvinyl alcohols, polyacrylamides, polyamides, polyacrylates, polyetheresters, polymethacrylates, polyurethanes, polycaprolactone, polyphophazenes, polyorthoesters, polyglycolide, copolymers of lysine and lactic acid, and copolymers of lysine-RGD and lactic acid, and the like, and copolymers of the same.

"Sponge" refers to microsponge Delivery System as technology for the controlled release of topical agents and consists of macroporous beads, typically 10-25 microns in diameter, loaded with active agent which is described for example in Embil K. et al J Microencapsul. 1996 September-October; 13(5):575-88.

"Micelle" refers to an aggregate of molecules comprising a polar region (hydrophilic) and an apolar region (hydrophobic), wherein the polar heads are grouped in contact with a surrounding aqueous solvent to form a hydrophilic layer, and the hydrophobic tails locate in the micelle center.

The terms micro-, and nanoparticles refer to particles whose size is defined according to the prefix micro, and nano-, as defined above. Said particles may be made of different materials such as glass, polymers (polyethylene, polystyrene), and ceramic materials.

The terms micro-, and nanospheres refer to spherical particles whose size is defined according to the prefix micro, and nano-, as defined above. Said spheres may be made of different materials such as glass, polymers (polyethylene, polystyrene), and ceramic materials.

The terms micro- and nanoemulsion refer to a homogeneous system that is formed by immiscible liquids (or liquids and particles), wherein one type of liquid or particles (dispersed phase) is dispersed in the other liquid(s) (continuous phase), and wherein the prefix micro- or nano-, as defined above, refer to the size of the dispersed phase.

Examples of hydrolyzed vegetal, animal or synthetic proteins are hydrolyzed wheat, oat, barley, corn, soy, bovine seroalbumin, silk, rice, milk, egg white, gelatin, among others.

In another preferred embodiment, the composition according to the invention is provided as a formulation selected from the group consisting of creams, emulsions, oils, milks, balsams, foams, lotions, gels, liniments, serums, soaps, shampoos, ointments, mousses, pomades, powders, bars, pencils, vaporizers, sprays, capsules, tablets, granules, chewing gums, solutions, suspensions, syrups, jellies and gelatins; or incorporated into a fabric selected from the group consisting of bandages, gauzes, t-shirts, tights, socks, underwear, girdles, gloves, diapers, sanitary napkins, dressings, bedspreads, wipes, hydrogels, adhesive patches, non-adhesive patches, and face masks.

In a third aspect, the invention refers to a compound of formula (I) as defined in the first aspect, or to a composition as defined in the second aspect, for use the prevention of bacterial and/or fungal growth when used to treat a human or animal. The inhibition of bacterial and/or fungal growth is an effective weapon in the prevention and/or treatment of infections.

In a fourth aspect, the invention refers to the use of a compound of formula (I) as defined in the first aspect, or composition as defined in the second aspect, for the manufacture of a medicament for the prevention of fungal and/or bacterial growth when administered to a human or animal.

In a fifth aspect, the invention relates to a method for the prevention of fungal and/or bacterial growth in a human or animal in need thereof, which comprises the administration of an effective amount of a compound of formula (I) as defined the first aspect, or composition as defined in the second aspect.

By an "effective amount" or a "therapeutically effective amount" of a drug or pharmacologically active agent is meant a nontoxic but sufficient amount of the drug or agent to provide the desired effect. The amount that is "effective" will vary from subject to subject, depending on the age and general condition of the subject, the particular active agent or agents, and the like. Thus, it is not always possible to specify an exact "effective amount". However, an appropriate "effective amount" in any individual case may be determined by one of ordinary skill in the art using routine experimentation.

In one embodiment the compound of formula (I) as defined in the first aspect, or the composition as defined in the second aspect may be used to prevent bacterial and/or fungal growth at body surfaces of a subject in need thereof such as the skin or mucous membranes by topical application to said surfaces.

In another embodiment the compound of formula (I) as defined in the first aspect, or the composition as defined in the second aspect may be used to prevent bacterial and/or fungal growth in a subject in need thereof by systemic administration to said subject, for example by enteral administration (absorption of the drug through the gastrointestinal tract) or by parenteral administration (injection, infusion, or implantation).

In a sixth aspect, the invention refers to the use of a compound of formula (I) as defined in the first aspect to prevent bacterial and/or fungal growth in a composition, preferably a pharmaceutical or a cosmetic composition or at an inanimate surface such as a medical device.

Abbreviations $Ac_2O$: Acetic anhydride
CFU: Colony-forming unit
EDTA: Ethylenediaminotetraacetic acid
DIPEA: N,N-Diisopropylethylamine
DCM: Dichloromethane
DHB: Dihydroxybenzoic acid
DMF: Dimethylformamide
Fmoc: Fluorenylmethyloxycarbonyl
HBTU: O-(Benzotriazol-1-yl)-N,N,N',N'-tetramethyluronium hexafluorophosphate
$IC_{50}$: Half maximal inhibitory concentration
MeOH: Methanol
MIC: Minimum inhibitory concentration
MRSA: Methicillin resistant *Staphylococcus aureus*
PEG: Polyethyleneglycol
RBC: Red blood cell
TFA: Trifluoroacetic acid
TIS: Triisopropylsilane

EXAMPLES

Examples 1 and 2

Solid-phase Synthesis of Compounds of Formula (I) Wherein $R_2$ is $NH_2$ and $R_1$ is Acetyl (Example 1) or $R_1$ is Palmitoyl (Example 2)

The peptide of Example 1 (a compound of formula (I) wherein $R_1$ is acetyl and $R_2$ is $NH_2$) and the peptide of Example 2 (a compound of formula (I) wherein $R_1$, is palmitoyl and $R_2$ is $NH_2$) were synthesized using the solid-phase methodology.

Chemical peptide synthesis starts at the C-terminal end of the peptide and ends at the N-terminus. Therefore, the first for the peptide of formula (I) aminoacid is Phe. Fmoc-Phe-OH (3 eq) was directly incorporated on the Fmoc-Rink-amide-AM resin (0.5 mmol/g) with HBTU (3 eq), DIPEA (6 eq) in DMF for 1 h. Washings were performed with DMF (5×30 s) and DCM (5×30 s). Kaiser test was used to verify that the coupling was successful. For the deprotection of the Fmoc group, the resin was solvated with DMF (5×30 s), treated with a solution of piperidine/DMF 20% (3×5 min) and finally washed with DMF (5×30 s) and DCM (5×30 s). Then, the resin was solvated with DMF (5×30 s).

The above described procedure was repeated 5 times to sequentially incorporate the following amino acids (in this order): Arg, Lys, Gln, Ala and Lys replacing Fmoc-Phe-OH by the corresponding Fmoc-AA-OH derivative where AA stands for the aminoacid to be incorporated. For the product of example 2 where $R_1$ is palmitoyl the process was repeated one more time using palmitic acid instead of a Fmoc-AA-OH derivative. For the product of example 1 where $R_1$ is acetyl the resin was solvated with DMF (5×30 s), treated with a mix $Ac_2O$ (10 eq), DIPEA (10 eq) in DMF for 15 min and washed with DMF (5×30 s) and DCM (5×30 s) Finally, the cleavage of the peptide from the resin was carried out by treating the resin with $TFA:TIS:H_2O$ (95:2.5:2.5) for 2 h, yielding the peptide of sequence HPLC: C18 column; UV 220 nm; flux 1 mL/min; gradient acetonitrile-water in 8 min.

Example 3

Solid-phase Synthesis of Compounds of Formula (I) Wherein $R_2$ is $NH-(CH_2)_3-(OCH_2CH_2)_3-CH_2-NH_2$ and $R_1$ is Palmitoyl The peptide of Example 3 (a compound of formula (I) wherein $R_1$, is palmitoyl and $R_2$ is $NH-(CH_2)_3-(OCH_2CH_2)_3-CH_2-NH_2$) were synthesized using the solid-phase methodology.

Chemical peptide synthesis starts at the C-terminal end of the peptide and ends at the N-terminus. A 2-Chlorotrityl chloride Resin (1 mmol) was functionalized by reacting the resin with 4,7,10-Trioxa-1,13-tridecanediamine indicated as $NH_2-(CH_2)_3-(OCH_2CH_2)_3-CH_2-NH_2$ (10 eq) in the presence of DCM for 45 min, later MeOH (0.8 mL/g resin) was added and left for 30 min. Washings were performed with DMF (5×30 s) and DCM (5×30 s). Then, the rest of aminoacids were incorporated with the method described in examples 1 and 2.

The peptides of examples 1 to 3 were characterized by reversed phase high performance liquid chromatography (RP-HPLC) in a Waters series 996 photodiode detector. This instrument was provided with a Waters 2695 modular separator and the Millenium program. The reversed phase column used was C18 column (symmetry C18 reversed phase HPLC columns, 4.6×150 mm, 5 μm) (Waters, Ireland). The peptides were detected at 220 nm, and a linear gradient of 5 to 100% acetonitrile (+0.036% TFA) and water (+0.045% TFA) was used for 8 minutes at a flow rate of 1.0 mL/min. The peptides were analyzed by matrix-assisted laser desorption/ionization mass spectroscopy and time-of-flight (MALDI-TOF) analysis, using a matrix of 2,5-dihydroxybenzoic acid (DHB) and a Micromass VG-quattro spectrometer. The peptides had a purity greater than 90% using RP-HPLC.

TABLE 1

Characterization of the peptides synthesized using RP-HPLC and HPLC-MS or MALDI-TOF. The exact mass was calculated using the software ChemDraw ®.

| # | Sequence | Retention time (RP-HPLC) (min) | Purity (RP-HPLC) (%) | Theoretical molecular weight (g/mol) | Experimental molecular weight (m + H/z) |
|---|---|---|---|---|---|
| Example 1 | Ac-KAQKRF-$NH_2$ (Ac-SEQ ID NO: 1-$NH_2$) | 3.0 | 98.96 | 817.91 | 818.40 |

TABLE 1-continued

Characterization of the peptides synthesized using RP-HPLC and HPLC-MS or MALDI-TOF. The exact mass was calculated using the software ChemDraw ®.

| # | Sequence | Retention time (RP-HPLC) (min) | Purity (RP-HPLC) (%) | Theoretical molecular weight (g/mol) | Experimental molecular weight (m + H/z) |
|---|---|---|---|---|---|
| Example 2 | Palm-KAQKRF-NH$_2$ (Palm-SEQ ID NO: 1-NH$_2$) | 6.1 | 93.59 | 1014.31 | 1014.62 |
| Example 3 | Palm-KAQKRF-NH—(CH$_2$)$_3$—(OCH$_2$CH$_2$)$_3$—CH$_2$—NH$_2$ (Palm-SEQ ID NO: 1-NH—(CH$_2$)$_3$—(OCH$_2$CH$_2$)$_3$—CH$_2$—NH$_2$) | 6.0 | 94.32 | 1217.29 | 1217.98 |

Example 1 (Ac-KAQKRF —NH$_2$) (Ac-SEQ ID NO: 1—NH$_2$) was synthesized using the solid-phase methodology described above and was obtained in a yield of 70% and a purity greater than 96.9%.

Example 2 (Palm-KAQKRF —NH$_2$) (Palm-SEQ ID NO: 1—NH$_2$) was synthesized using the solid-phase methodology described above and was obtained in a yield of 74% and a purity greater than 93.5%.

Example 3 (Palm-KAQKRF —NH—(CH$_2$)$_3$—(OCH$_2$CH$_2$)$_3$—CH$_2$—NH$_2$) (Palm-SEQ ID NO: 1—NH—(CH$_2$)$_3$—(OCH$_2$CH$_2$)$_3$—CH$_2$—NH$_2$ was synthesized using the solid-phase methodology described above and was obtained in a yield of 98% and a purity greater than 94.32%.

Example 4

Minimum Inhibitory Concentration (MIC) of the Compounds of Example 1 to 3

Minimum inhibitory concentration (MIC) is the lowest concentration of an antimicrobial that will inhibit the growth occurred between time zero and 24 h.

The MIC of peptides of examples 1, 2 and 3 was determined using gram negative bacteria (*Escherichia Coli, Vibrio angillarum, Vibrio ordalii, Enterobacter aerogenes, Aeromonas hydrophila, Vibrio parahemolyticus, Bacillus Oleronius* and *Salmonella tiphy*) and gram positive bacteria (*Bacillus megaterium, Micrococcus luteus, Staphylococcus aureus* and *Staphylococcus epidermidis*).

To initiate the exponential phase of bacterial growth prior to the assay, a sample of each bacteria type was allowed to grow overnight at 37° C. in Mueller-Hinton broth and incubated at 37° C. MRSA (Methicillin Resistant *Staphylococcus aureus*) was grown at 35° C. in cation-adjusted MH broth.

A final concentration of 1×10$^5$ CFU/ml was used in all assays. The assays were carried out in 96-well flat-bottom plates. Bacterial suspension in 2× concentrated broth was added to the different peptides at concentrations that varied from 2.500 to 1 µ/mL in H$_2$O in serial twofold dilutions (Time t$_0$). The plates were then incubated for 21 h (Time t$_f$) at 37° C. The relative percent growth of the bacteria for each peptide as determined by measuring the optical density at 620 nm, was consistent in three separate determinations. The concentration necessary to inhibit 50% bacterial growth (IC$_{50}$) could be by using sigmoidal curve-fitting software. The MICs were defined as the lowest concentrations of peptides at which total inhibition of growth is observed and no change in optical density at 620 nm occurred between the measures obtained at t$_0$ and t$_f$.

TABLE 2

| | Gram negative bacteria MIC (µg/ml) | | | | | | |
|---|---|---|---|---|---|---|---|
| Compound Example | E. Coli | Vibrio parahemolyticus | Vibrio angillarum | Vibro ordalii | Enterobacter hydrophila | Salmonella tiphy | Bacillus oleronius |
| 1 | 10.8 | 9.4 | 31.2 | 10.2 | 14.2 | 11.7 | 11.9 |
| 2 | 5.6 | 6.0 | 31.0 | 7.4 | 11.3 | 6.1 | 9.7 |
| 3 | 5.5 | 6.2 | 30.0 | 8.2 | 11.6 | 5.8 | 8.0 |

TABLE 3

| | Gram positive bacteria MIC (µg/ml) | | | |
|---|---|---|---|---|
| Compound Example | Micrococcus luteus | Bacillus megaterium | Staphylococcus aureus | Staphylococcus epidermidis |
| 1 | 6.0 | 13.7 | 11.7 | 11.4 |
| 2 | 5.6 | 12.3 | 5.7 | 5.6 |
| 3 | 5.5 | 12.1 | 5.5 | 5.8 |

As shown in Tables 2 and 3, peptides of examples 1, 2 and 3 showed minimum inhibitory concentrations in the order of 5-35 µg/ml against a variety of Gram-negative bacteria and in the order of 5-15 µg/ml against a variety of Gram-positive bacteria allowing the use of this compound to inhibit growth of both Gram-negative bacteria and Gram-positive bacteria.

Example 5

Minimum Inhibitory Concentration (MIC) of the Compounds of Examples 1 to 3 for Fungi For this essay, diluted spores kept at −80° C. were used (fresh ones in the case of de *Saprolegnia* sp.), 1×10$^4$ spores/ml at the specific media for every fungi. 10 µg/ml of tetracycline were added to avoid bacterial action. 20 µg of peptide solution plus 80 µg of spore solution alongside the adequated media are added to a 96 wells microplaque. As a positive control a culture of the spores at the same concentration than the assay but without peptide. The MICs were defined as the lowest concentrations of peptides at which total inhibition of growth is observed and no change in optical density at 595 nm occurred between the measures obtained at $t_0$ and $t_f$.

TABLE 4

| Compound Example | MIC (µg/ml) | | |
|---|---|---|---|
| | *Fusarium oxysporum* | *Neurospora crassa* | *Saprolegnia* sp |
| 1 | 0.9 | 0.9 | 0.2 |
| 2 | 0.5 | 0.2 | 0.1 |
| 3 | 0.4 | 0.3 | 0.1 |

As shown in Table 4, peptides of examples 1, 2 and 3 showed minimum inhibitory concentrations in the order 0.1-0.5 µg/ml against a variety of fungi, allowing the use of these compounds to inhibit fungal growth.

Example 6

Hemolytic Assay

As a safety test for the peptides of the present invention the hemolytic activity was determined by using human erythrocytes (RBCs).

The assays were carried out in 96-well flat-bottom plates against a 0.25% RBC suspension as described elsewhere (Blondelle, S. E., L. R. Simpkins, E. Pérez-Payá, and R. A. Houghten. 1993. Influence of tryptophan residues on melitin's hemolytic activity. Biochim. Biophys. Acta 1202:331-336.).

In brief, peptide mixtures were added to the RBC solution at concentrations that varied from 500 to 4 µg/mL in serial twofold dilutions. Following incubation at 37° C. for 1 hour, the plates were centrifuged at 2.800 rpm for 5 min. The supernatant was separated from the pellet, an its optical density at 414 nm was measured. The hemolytic dose to lyse 50% of RBCs ($IC_{50}$) was calculated by using the sigmoidal curve-fitting software Graphpad.

TABLE 5

| Example | $IC_{50}$ (µg/ml) Human erythrocytes |
|---|---|
| 1 | >500 |
| 2 | >500 |
| 3 | >500 |

Example 7

LPS-Neutralizing Activity

The LPS-neutralizing activity of the peptides of Examples 1, 2 and 3, and a variety of peptides (comparative examples 1-6) was determined. The peptides of comparative examples 1-6 were synthesized following the methodology described above for Example 1. The chemical structures of these peptides is provide in Table 6.

All solutions used in the LPS-neutralizing activity assay were tested to ensure they were endotoxin-free and material was sterilized by heating 3 h at 180° C. LPS from *E. Coli* 055:B5 and Polymyxin B were purchased from Sigma. LPS-neutralizing activity was measured using the chromogenic Limulus Amebocyte Lysate (LAL) test 40 following the manufacturer's instructions (Cambrex). LAL reagent contains a clottable protein that is activated in the presence of non-neutralized LPS and is an extremely sensitive indicator of the presence of endotoxin. When activated, this enzyme catalyses the release of p-nitroaniline (pNA) from the colorless chromogenic substrate Ac-Ile-Glu-Ala-Arg-pNA. The pNA released was measured photometrically at 405 nm in a Rosys Anthos 2010 microtiter plate reader (Tecnomara AG, Zurich, Switzerland). Peptides were incubated at a range of concentrations (200 to 0.001 µM) with LPS (100 pg/mL) in a 96-well microtiter for 45 min at 37° C. Polymyxin B (10 µg/mL) was used as positive control. LAL (12.5 µL) was added to start the reaction at 37° C. After 16 min, non-neutralized LPS was detected after a 10 min incubation with the chromogenic substrate (25 µ) Acetic acid (25% v/v final concentration) was added to stop the reaction and the absorbance was monitored at 405 nm in a Multiskan Ascent microtiter plate reader (ThermoLabsystems). $IC_{50}$ (the concentration necessary to in vitro neutralize 50% of LPS) values were determined by a serial dilution assay using 100 pg/mL of LPS and a range of peptide concentrations as mentioned above.

TABLE 6

Peptide sequences and LPS-neutralization activity ($IC_{50}$).

| # | Sequence | $IC_{50}$ (µM) ± SD |
|---|---|---|
| Example 1 | Ac-KAQKRF-NH$_2$ (Ac-SEQ ID NO: 1-NH$_2$) | 18 ± 1.0 |
| Example 2 | Palm-KAQKRF-NH$_2$ (Palm-SEQ ID NO: 1-NH$_2$) | 11 ± 1.0 |
| Example 3 | Palm-KAQKRF-NH-(CH$_2$)$_3$-(OCH$_2$CH$_2$)$_3$-CH$_2$-NH$_2$ (Palm-SEQ ID NO: 1-NH-(CH$_2$)$_3$-(OCH$_2$CH$_2$)$_3$-CH$_2$-NH$_2$) | 4 ± 1.2 |
| Comparative Example 1 | Ac-IKISGKWKAQKRFLKM-NH$_2$ (Ac-SEQ ID NO: 2-NH$_2$) | 34 ± 1.3 |
| Comparative Example 2 | Ac-IKISGK-NH$_2$ (Ac-SEQ ID NO: 3-NH$_2$) | 105 ± 1.2 |
| Comparative Example 3 | Ac-KISGKW-NH$_2$ (Ac-SEQ ID NO: 4-NH$_2$) | 96 ± 1.1 |
| Comparative Example 4 | Ac-SGKWKA-NH$_2$ (Ac-SEQ ID NO: 5-NH$_2$) | 85 ± 1.4 |
| Comparative Example 5 | Ac-KWKAQK-NH$_2$ (Ac-SEQ ID NO: 6-NH$_2$) | 47 ± 1.1 |
| Comparative Example 6 | Ac-AQKRFL-NH$_2$ (Ac-SEQ ID NO: 7-NH$_2$) | 46 ± 1.1 |

As known in the art, the LPS-neutralization ability is related to the antimicrobial activity. Peptides of examples 1, 2 and 3 (which correspond to subsequences of the peptide described in comparative example 1) present $IC_{50}$ values of 18 (±1.0), 11 (±1.0) µM, and 4 (±1.2) µM respectively, surprisingly being more active than the peptide of comparative example 1 (having a length of 16 amino acids). In contrast, other hexapeptides (also corresponding to subsequences of the peptide described in comparative example 1) showed and $IC_{50}$ greater than 45 µM, thus having the expected lower activity than the peptide of comparative example 1 (having a length of 16 amino acids).

The invention claimed is:

1. A compound of formula (I):

R$_1$-Lys-Ala-Gln-Lys-Arg-Phe-R$_2$ (R$_1$-SEQ ID NO: 1-R$_2$)

wherein

R$_1$ is selected from the group consisting of H, C$_1$-C$_{24}$ alkyloyl, C$_2$-C$_{24}$ alkenyloyl, and C$_6$-C$_{10}$ aryl;

R$_2$ is selected from the group consisting of —OR$_3$, —SR$_3$, —NR$_3$R$_4$, and NH—(CH2)$_3$-(OCH$_2$CH$_2$)$_n$—CH$_2$—NH$_2$ wherein n is an integer from 1 to 6;

R$_3$ and R$_4$ are independently selected from the group consisting of H; C$_1$-C$_6$ alkyl; C$_3$-C$_8$ cycloalkyl; C$_6$-C$_{10}$ aryl; C$_6$-C$_{10}$ aryl-C$_1$-C$_6$ alkyl; 5, 6 or 7 membered heterocycle containing 1, 2 or 3 heteroatoms in the ring independently selected from the group consisting of N, O and S; 5 or 6 membered monocyclic heteroaryl containing 1, 2, 3 or 4 heteroatoms in the ring independently selected from the group consisting of N, O and S;

8, 9 or 10 membered bicyclic heteroaryl containing 1, 2, 3 or 4 heteroatoms independently selected from the group consisting of N, O and S; and heteroaryl-C$_1$-C$_3$-alkyl, wherein the heteroaryl is a 5 or 6 membered monocyclic heteroaryl containing 1, 2, 3 or 4 heteroatoms in the ring independently selected from the group consisting of N, O and S or a 8, 9 or 10 membered bicyclic heteroaryl containing 1, 2, 3 or 4 heteroatoms independently selected from the group consisting of N, O and S;

its stereoisomers, its cosmetically acceptable salts, or mixtures thereof.

2. The compound according to claim 1 wherein R$_1$ is selected from the group consisting of H, acetyl, C$_{10}$-C$_{24}$ alkyloyl and C$_{10}$-C$_{24}$ alkenyloyl.

3. The compound according to claim 2 wherein R$_1$ is selected from the group consisting of caproyl (CH$_3$—(CH$_2$)$_8$—C(O)—), lauroyl (CH$_3$—(CH$_2$)$_{10}$—C(O)—), myristoyl (CH$_3$—(CH$_2$)$_{12}$—C(O)—), palmitoyl (CH$_3$—(CH$_2$)$_{14}$—C(O)—, stearoyl (CH$_3$—(CH$_2$)$_{16}$—C(O)—), arachidoyl (CH$_3$—(CH$_2$)$_{18}$—C(O)—) and behenoyl (CH$_3$—(CH$_2$)$_{20}$—C(O)—).

4. The compound according to claim 3 wherein R$_1$ is selected from the group consisting of acetyl and palmitoyl.

5. The compound according to claim 1 wherein R$_2$ is selected from the group consisting of —OR$_3$, —SR$_3$, and —NR$_3$R$_4$, wherein R$_3$ and R$_4$ are independently selected from the group consisting of H, C$_1$-C$_6$ alkyl, and —NH—(CH$_2$)$_3$—(OCH$_2$CH$_2$)$_n$—CH$_2$—NH$_2$ wherein n is an integer from 1 to 6.

6. The compound according to claim 5 wherein R$_2$ is selected from the group consisting of —OH, —SH, —NH$_2$ and —NH—(CH$_2$)$_3$—(OCH$_2$CH$_2$)$_n$—CH$_2$—NH$_2$ wherein n is an integer from 1 to 6.

7. The compound according to claim 6 wherein R$_2$ is NH$_2$ or —NH—(CH$_2$)$_3$—(OCH$_2$CH$_2$)$_3$—CH$_2$—NH$_2$.

8. The compound according to claim 1 wherein the compound is one of:

(Palm-SEQ ID NO: 1-NH$_2$)
Palm-Lys-Ala-Gln-Lys-Arg-Phe-NH$_2$;

(Ac-SEQ ID NO: 1-NH$_2$)
Ac-Lys-Ala-Gln-Lys-Arg-Phe-NH$_2$;

and (Palm-SEQ ID NO: 1-NH-(CH$_2$)$_3$-(OCH$_2$CH$_2$)$_3$-CH$_2$-NH$_2$)
Palm-Lys-Ala-Gln-Lys-Arg-Phe-NH-(CH$_2$)$_3$-(OCH$_2$CH$_2$)$_3$-CH$_2$-NH$_2$.

9. A composition which comprises a compound according to claim 1 and optionally one or more cosmetically acceptable excipient(s).

10. The composition according to claim 9, wherein the one or more cosmetically acceptable excipient(s) is selected from the group consisting of humectants, emollients, rheological modifiers, perfumes, essential oils, preserving agents, solvents, emulsifiers, silicones, antioxidants, chelating agents, vitamins, and mixtures of two or more of the foregoing.

11. The composition according to claim 9, wherein the compound of formula (I) represents from 0.0001% to 5% by weight with respect to the total weight of the composition.

12. The composition according to claim 9, wherein the compound of formula (I) is incorporated into a cosmetically acceptable vehicle or sustained release system selected from the group consisting of liposomes, millicapsules, microcapsules, nanocapsules, sponges, vesicles, micelles, millispheres, microspheres, nanospheres, microemulsions, nanoemulsions, milliparticles, microparticles, nanoparticles, and solid lipid nanoparticles, are incorporated into hydrolyzed vegetal, animal or synthetic proteins, or are adsorbed onto a cosmetically acceptable solid support selected from the group consisting of talc, bentonite, silica, starch and maltodextrin, dextran and its derivatives.

13. The composition according to claim 9, wherein said composition is provided in a formulation selected from the group consisting of creams, emulsions, oils, milks, balsams, foams, lotions, gels, liniments, serums, soaps, shampoos, ointments, mousses, pomades, powders, bars, pencils, vaporizers, sprays, capsules, tablets, granules, chewing gums, solutions, suspensions, syrups, jellies and gelatins.

14. A method for the prevention of fungal and/or bacterial growth in a human or animal in need thereof, which comprises the administration of an effective amount of a compound of formula (I) as defined in claim 1.

15. A method of preventing fungal and/or bacterial growth in a composition or at an inanimate surface, said method comprising adding to said composition and/or said inanimate surface a compound of formula (I) as defined in claim 1.

16. A method for the prevention of fungal and/or bacterial growth in a human or animal in need thereof, said method comprising administering to said human or animal an effective amount of a composition as defined in claim 9.

17. The compound of claim 1, wherein:
$R_1$ is selected from the group consisting of H, acetyl, $C_{10}$-$C_{24}$ alkyloyl and $C_{10}$-$C_{24}$ alkenyloyl; and
$R_2$ is selected from the group consisting of —$OR_3$, —$SR_3$, and —$NR_3R_4$, wherein $R_3$ and
$R_4$ are independently selected from the group consisting of H, $C_1$-$C_6$ alkyl, and —NH—$(CH_2)_3$—$(OCH_2CH_2)_n$—$CH_2$—$NH_2$ wherein n is an integer from 1 to 6.

18. The method of claim 14, wherein:
$R_1$ is selected from the group consisting of H, acetyl, $C_{10}$-$C_{24}$ alkyloyl and $C_{10}$-$C_{24}$ alkenyloyl; and
$R_2$ is selected from the group consisting of —$OR_3$, —$SR_3$, and —$NR_3R_4$, wherein $R_3$ and
$R_4$ are independently selected from the group consisting of H, $C_1$-$C_6$ alkyl, and —NH—$(CH_2)_3$—$(OCH_2CH_2)_n$—$CH_2$—$NH_2$ wherein n is an integer from 1 to 6.

19. The method of claim 15, wherein:
$R_1$ is selected from the group consisting of H, acetyl, $C_{10}$-$C_{24}$ alkyloyl and $C_{10}$-$C_{24}$ alkenyloyl; and
$R_2$ is selected from the group consisting of —$OR_3$, —$SR_3$, and —$NR_3R_4$, wherein $R_3$ and
$R_4$ are independently selected from the group consisting of H, $C_1$-$C_6$ alkyl, and —NH—$(CH_2)_3$—$(OCH_2CH_2)_n$—$CH_2$—$NH_2$ wherein n is an integer from 1 to 6.

20. The method of claim 16, wherein:
$R_1$ is selected from the group consisting of H, acetyl, $C_{10}$-$C_{24}$ alkyloyl and $C_{10}$-$C_{24}$ alkenyloyl; and
$R_2$ is selected from the group consisting of —$OR_3$, —$SR_3$, and —$NR_3R_4$, wherein $R_3$ and
$R_4$ are independently selected from the group consisting of H, $C_1$-$C_6$ alkyl, and —NH—$(CH_2)_3$—$(OCH_2CH_2)_n$—$CH_2$—$NH_2$ wherein n is an integer from 1 to 6.

21. The composition according to claim 9, wherein the composition is incorporated into a fabric selected from the group consisting of bandages, gauzes, t-shirts, tights, socks, underwear, girdles, gloves, diapers, sanitary napkins, dressings, bedspreads, wipes, hydrogels, adhesive patches, non-adhesive patches, and face masks.

\* \* \* \* \*

SEQUENCE LISTING

<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: formula (I)

<400> SEQUENCE: 1

Lys Ala Gln Lys Arg Phe
1               5

<210> SEQ ID NO 2
<211> LENGTH: 16
<212> TYPE: PRT
<213> ORGANISM: Artificial Sequence
<220> FEATURE:
<223> OTHER INFORMATION: Comparative example 1

<400> SEQUENCE: 2

Ile Lys Ile Ser Gly Lys Trp Lys Ala Gln Lys Arg Phe Leu Lys Met
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: Comparative example 2

<400> SEQUENCE: 3

Ile Lys Ile Ser Gly Lys
1               5

<210> SEQ ID NO 4
<211> LENGTH: 6
<212> TYPE: PRT
<213> ORGANISM: Artificial Sequence
<220> FEATURE:
<223> OTHER INFORMATION: Comparative example 3

<400> SEQUENCE: 4

Lys Ile Ser Gly Lys Trp
1               5

<210> SEQ ID NO 5
<211> LENGTH: 6
<212> TYPE: PRT
<213> ORGANISM: Artificial Sequence
<220> FEATURE:
<223> OTHER INFORMATION: Comparative example 4

<400> SEQUENCE: 5

Ser Gly Lys Trp Lys Ala
1               5

<210> SEQ ID NO 6
<211> LENGTH: 6
<212> TYPE: PRT
<213> ORGANISM: Artificial Sequence
<220> FEATURE:
<223> OTHER INFORMATION: Comparative example 5

<400> SEQUENCE: 6

Lys Trp Lys Ala Gln Lys
1               5

```
<210> SEQ ID NO 7
<211> LENGTH: 6
<212> TYPE: PRT
<213> ORGANISM: Artificial Sequence
<220> FEATURE:
<223> OTHER INFORMATION: Comparative example 6

<400> SEQUENCE: 7

Ala Gln Lys Arg Phe Leu
1               5
```